United States Patent
Kim et al.

(10) Patent No.: US 8,426,570 B2
(45) Date of Patent: Apr. 23, 2013

(54) RECOMBINANT EXPRESSION VECTOR FOR ANIMAL CELL

(75) Inventors: Keun Soo Kim, Daejeon (KR); Hye Kyung Ju, Daejeon (KR); Choon Ju Jeon, Daejeon (KR); Jae Seob Kim, Daejeon (KR)

(73) Assignee: Aprogen Inc., Daejeon (KR)

( * ) Notice: Subject to any disclaimer, the term of this patent is extended or adjusted under 35 U.S.C. 154(b) by 94 days.

(21) Appl. No.: 13/002,814

(22) PCT Filed: Jul. 7, 2009

(86) PCT No.: PCT/KR2009/003714
§ 371 (c)(1),
(2), (4) Date: Jan. 6, 2011

(87) PCT Pub. No.: WO2010/005227
PCT Pub. Date: Jan. 14, 2010

(65) Prior Publication Data
US 2011/0117643 A1     May 19, 2011

(30) Foreign Application Priority Data
Jul. 10, 2008 (KR) .................. 10-2008-0066771

(51) Int. Cl.
*C07H 21/02* (2006.01)
*C07H 21/04* (2006.01)
*C12N 5/00* (2006.01)
*C12N 5/02* (2006.01)
*C12N 15/00* (2006.01)

(52) U.S. Cl.
USPC ................ 536/23.1; 435/325; 435/455

(58) Field of Classification Search ............. 536/23.1
See application file for complete search history.

(56) References Cited

U.S. PATENT DOCUMENTS

| | | | |
|---|---|---|---|
| H2181 H | 2/2007 | Levinson et al. | |
| 7,846,724 B2 | 12/2010 | Hansen et al. | |
| 7,867,491 B2 * | 1/2011 | Yang et al. | 424/130.1 |
| 2005/0176099 A1 * | 8/2005 | Saha | 435/69.1 |
| 2010/0120089 A1 | 5/2010 | Choi et al. | |

OTHER PUBLICATIONS

Huang, 1998, PNAS, vol. 95, pp. 14669-14674.*
Genbank NM_010049.3, Jun 28, 2012, http://www.ncbi.nlm.nih.gov/nuccore/NM_010049.3.*
Chen, Jour Biol Chem, 259:3933-3943, 1984.*
Bai et al., "Expression of Human-Mouse Chimeric Antibody ch-BD1 and its Affinity to Human Bladder Cancer in Vitro and in Vivo," Zhonghua Yi Xue Za Zhi 83:333-337, 2003.
International Search Report from International Application No. PCT/KR2009/003714, dated Feb. 18, 2010 (date of completion of search) and Feb. 19, 2010 (date of mailing of report).

* cited by examiner

*Primary Examiner* — Valarie Bertoglio
(74) *Attorney, Agent, or Firm* — Clark & Elbing LLP (57) ABSTRACT

The present invention relates to a recombinant expression vector for an animal cell containing a dihydrofolate reductase (DHFR) coding nucleotide sequence operatively linked to a DHFR promoter, to an animal cell line transformed by the vector, and to a method for preparing a target protein using the same. As compared with existing animal cell expression vectors, the vector of the present invention enables an effective screening of a cell line clone in which foreign genes are amplified together with DHFR genes even at a much lower methotrexate concentration. The present invention exhibits excellent effects in cell line preparation as high-productivity cell lines can be ensured in a short time through the use of a lower concentration of methotrexate in the process of protein production cell line establishment.

9 Claims, 9 Drawing Sheets

Figure 1a

SEQ ID NO: 1

5'-ACTAGAGCAT TGGGGGGGGG GACAGCTCAG GGCTGCGATT TCGCGCCAAA

CTTGACGGCA ATCCTAGCGT GAAGGCTGGT AGGATTTTAT CCCCGCTGCC

ATCATGGTTC GACCATTGAA CTGCATCGTC GCCGTGTCCC AAAAT-3'

Figure 1b

SEQ ID NO: 2

5'-ACAGCTCAGG GCTGCGATTT CGCGCCAAAC TTGACGGCAA TCCTAGCGTG

AAGGCTGGTA GGATTTTATC CCCGCTGCCA TCATGGTTCG ACCATTGAAC

TGCATCGTCG CCGTGTCCCA AAAT-3'

SEQUENCE LISTING

<160> NUMBER OF SEQ ID NOS: 15

<210> SEQ ID NO 1
<211> LENGTH: 145
<212> TYPE: DNA
<213> ORGANISM: Mouse

<400> SEQUENCE: 1

```
actagagcat tggggggggg gacagctcag ggctgcgatt tcgcgccaaa cttgacggca        60
atcctagcgt gaaggctggt aggattttat ccccgctgcc atcatggttc gaccattgaa       120
ctgcatcgtc gccgtgtccc aaaat                                             145
```

<210> SEQ ID NO 2
<211> LENGTH: 124
<212> TYPE: DNA
<213> ORGANISM: Mouse

<400> SEQUENCE: 2

```
acagctcagg gctgcgattt cgcgccaaac ttgacggcaa tcctagcgtg aaggctggta        60
ggattttatc cccgctgcca tcatggttcg accattgaac tgcatcgtcg ccgtgtccca       120
aaat                                                                    124
```

<210> SEQ ID NO 3
<211> LENGTH: 564
<212> TYPE: DNA
<213> ORGANISM: Homo sapiens
<220> FEATURE:
<221> NAME/KEY: gene
<222> LOCATION: (1)..(564)
<223> OTHER INFORMATION: dihydrofolate reductase (DHFR)

<400> SEQUENCE: 3

```
atggttggtt cgctaaactg catcgtcgct gtgtcccaga acatgggcat cggcaagaac        60
ggggacctgc cctggccacc gctcaggaat gaattcagat atttccagag aatgaccaca       120
acctcttcag tagaaggtaa acagaatctg gtgattatgg gtaagaagac ctggttctcc       180
```

```
attcctgaga agaatcgacc tttaaagggt agaattaatt tagttctcag cagagaactc    240
aaggaacctc cacaaggagc tcattttctt tccagaagtc tagatgatgc cttaaaactt    300
actgaacaac cagaattagc aaataaagta gacatggtct ggatagttgg tggcagttct    360
gtttataagg aagccatgaa tcacccaggc catcttaaac tatttgtgac aaggatcatg    420
caagactttg aaagtgacac gttttttcca gaaattgatt tggagaaata taaacttctg    480
ccagaatacc caggtgttct ctctgatgtc caggaggaga aaggcattaa gtacaaattt    540
gaagtatatg agaagaatga ttaa                                           564
```

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4

```
tcgaagcttg atggcagcgg ggataa                                          26
```

<210> SEQ ID NO 5
<211> LENGTH: 26
<212> TYPE: DNA
<213> ORGANISM: Artificial Sequence
<220> FEATURE:
<223> OTHER INFORMATION: Synthetic Construct

<400> SEQUENCE: 5

```
gggctcgagt aagcattggg gggggg                                          26
```

<210> SEQ ID NO 6
<211> LENGTH: 26
<212> TYPE: DNA
<213> ORGANISM: Artificial Sequence
<220> FEATURE:
<223> OTHER INFORMATION: Synthetic Construct

<400> SEQUENCE: 6

```
gataagcttc gaaaaaggat atacaa                                          26
```

<210> SEQ ID NO 7
<211> LENGTH: 26
<212> TYPE: DNA
<213> ORGANISM: Artificial Sequence
<220> FEATURE:
<223> OTHER INFORMATION: Synthetic Construct

<400> SEQUENCE: 7

```
caactcgagc atctcaatta gtcagc                                          26
```

<210> SEQ ID NO 8
<211> LENGTH: 26
<212> TYPE: DNA
<213> ORGANISM: Artificial Sequence
<220> FEATURE:
<223> OTHER INFORMATION: Synthetic Construct

<400> SEQUENCE: 8

```
ccactcgagc caggcaggca gaagta                                          26
```

<210> SEQ ID NO 9
<211> LENGTH: 26
<212> TYPE: DNA
<213> ORGANISM: Artificial Sequence
<220> FEATURE:

<223> OTHER INFORMATION: Synthetic Construct

<400> SEQUENCE: 9
cccaaaatat ggggattggc aagaac                                    26

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
gggggatccg acatgataag atacat                                    26

<210> SEQ ID NO 11
<211> LENGTH: 45
<212> TYPE: DNA
<213> ORGANISM: Artificial Sequence
<220> FEATURE:
<223> OTHER INFORMATION: Synthetic Construct

<400> SEQUENCE: 11
gggggattca ctagagcatt gggggggggg acagctcagg gctgc                45

<210> SEQ ID NO 12
<211> LENGTH: 26
<212> TYPE: DNA
<213> ORGANISM: Artificial Sequence
<220> FEATURE:
<223> OTHER INFORMATION: Synthetic Construct

<400> SEQUENCE: 12
ccaatcccca tattttggga cacggc                                    26

<210> SEQ ID NO 13
<211> LENGTH: 26
<212> TYPE: DNA
<213> ORGANISM: Artificial Sequence
<220> FEATURE:
<223> OTHER INFORMATION: Synthetic Construct

<400> SEQUENCE: 13
gggggatcca cagctcaggc tgcgat                                    26

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14
tgcatctaga tattctatag tgtcac                                    26

<210> SEQ ID NO 15
<211> LENGTH: 27
<212> TYPE: DNA
<213> ORGANISM: Artificial Sequence
<220> FEATURE:
<223> OTHER INFORMATION: Synthetic Construct

<400> SEQUENCE: 15
ccccagctgg ttctttccgc ctcagaa                                   27

RECOMBINANT EXPRESSION VECTOR FOR ANIMAL CELL

CROSS-REFERENCE TO RELATED APPLICATIONS

This application is the U.S. national stage filing under 35 U.S.C. §371 of international application PCT/KR2009/003714, filed Jul. 7, 2009, which claims benefit of Korean Patent Application 10-2008-0066771, filed Jul. 10, 2008.

FIELD OF THE INVENTION

The present invention relates to a recombinant expression vector for an animal cell, to a cell line transformed by the vector, and to a method for preparing a target protein using the same.

BACKGROUND ART

In general, animal cell culture is a preferred technique in the industry for overexpressing the target protein. Because proteins with industrial value are mostly human or animal derived proteins, and specific protein modification mechanisms (glycosylation, phosphorylation, amidation) are carried out easily in animal cells. The animal cells currently used in industry are CHO (Chinese Hamster Ovary), BHK (Baby Hamster Kidney) and myeloma cells, where the target protein is expressed by transfecting expression vector into the cells, similar to the microorganism based expression system.

However, animal cells have a disadvantage of showing low level of transfected foreign gene expression compared to an expression in the microorganism. The system widely used in the industry to overcome this disadvantage is the foreign gene amplification system, which uses dihydrofolate reductase (DHFR) gene and its gene activation inhibitor, methotrexate (MTX). This system is based on the phenomenon of the DHFR gene required for the survival and the foreign gene located close by being amplified together. In detail, the gene coding for the target protein and gene coding for the selective marker, DHFR protein, that are inserted in the same region of the chromosomal DNA are amplified simultaneously when the concentration of MTX is increased artificially.

It has been previously reported that the gene located near the DHFR gene in the expression vector is amplified simultaneously when treated with MTX (Kaufman et al. *Mol Cell Biol. July;* 5(7):1750-9(1985)). There is a report of high level of a foreign gene being co-expressed in the animal cell when it is inserted in the vicinity of the DHFR gene in the expression vector (Alt et al. *Cold Spring Hath Symp Quant Biol.* 42 Pt 2:649-57(1978); U.S. Pat. No. 4,656,134).

Gene amplification is generally a very rare phenomenon, but there are indications that acquiring gene amplified cells could be achieved through selecting cells that are resistant to the serially increased MTX concentration. It takes about 3-4 weeks for the MTX resistant colonies to form, and several multiple steps of amplification process to achieve industrially significant levels of amplification using MTX concentrations ranging from 50 nM to 500 mM.

However, during the process of inducing gene amplification using MTX treatment, problems such as reduction in cell growth rate and in productivity may occur. For instance, there is a report indicating a decrease in the level of the recombinant protein expression, rather than an increase, despite the increase in MTX concentration (Kaufman et al. *Mol Cell Biol. J;*5(7):1750-9(1985)). Similarly, there is a case report of significantly increasing the gene amplification effect of MTX by mutating the DHFR gene control factor sequence in the expression vector (Bai et al. *Zhonghua Yi Xue Za Zhi.* February 25; 83 (4):333-7(2003)).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

The present inventors have performed intensive research to solve the problems when expressing protein using animal cell transformed with DHFR gene containing vector, such as the low level of expression and decrease in cell growth rate and in productivity by high concentrations of methotrexate. As a result, the present inventors developed a recombinant expression vector for acquiring large amounts of foreign protein by using a recombinant vector containing human derived DHFR gene operatively connected to the mouse derived DHFR promoter. This process can effectively amplify the foreign gene at a lower concentration of methotrexate, and thus completed the present invention.

Accordingly, it is an object of the present invention to provide a recombinant vector for a dhfr⁻ animal cell.

It is another object of this invention to provide a dhfr⁻ animal cell line transfected by the vector.

It is still another object of this invention to provide a method for preparing the protein using the transfected dhfr⁻ animal cell line.

Other objects and advantages of the present invention will become apparent from the detailed description to follow and together with the appended claims and drawings.

According to an aspect of this invention, the present invention provides (a) a dihydrofolate reductase (DHFR) promoter comprising nucleotide sequence listed in SEQ ID NO: 1 or SEQ ID NO: 2; and (b) a recombinant vector for a dhfr⁻ animal cell comprising DHFR-coding nucleotide sequence operatively linked to the promoter.

The present inventors have performed intensive research to solve the problems when expressing protein using animal cell transformed with DHFR gene containing vector, such as the low level of expression and decrease in cell growth rate and in productivity by high concentrations of methotrexate. As a result, the present inventors developed a recombinant expression vector for acquiring large amounts of foreign protein by using a recombinant vector containing human derived DHFR gene operatively connected to the mouse derived DHFR promoter. This process can effectively amplify the foreign gene at a lower concentration of methotrexate.

The term "DHFR (Dihydrofolate reductase)" used herein refers to an enzyme that reduces dihydrofolic acid to tetrahydrofolic acid, which is a key enzyme for nucleic acid synthesis and an essential enzyme for cell growth.

The present invention relates to an expression vector for producing large amounts of foreign protein in a dhfr⁻ animal cell under low concentration of DHFR inhibitor, particularly under a low concentration of methotrexate (MTX).

As used herein, "dhfr⁻ animal cell" refers to a transformed animal cell without or almost any DHFR enzyme activity in the cell by lack of normal DHFR expression. This invention is directed to using gene amplification principle of the gene including DHFR gene, to use as host cell character and host cell selection. That is, dhfr⁻ animal cell is transformed by dhfr gene containing vector, and then the transformed cell is treated with DHFR inhibitor. The cells amplified with high numbers of dhfr containing vectors are selected. Therefore, the vector amplification is achieved.

As used herein, "MTX (methotrexate)" refers to a DHFR inhibitor, which inhibits the reduction of folic acid to dihydrofolate ($FH_2$) and then to tetrahydrofolate ($FH_4$).

According to a preferred embodiment, the DHFR promoter is mouse derived, and the DHFR-coding nucleotide is human derived.

The DFHR promoter used in this invention is a partial sequence from the promoter of mouse dhfr gene which has the promoter activity suitable to the purpose of the present invention. The SEQ ID NO: 1 and SEQ ID NO: 2 promoters used in the present invention showed relatively low promoter activity compared to the conventional animal cell expression vectors. This leads to a reduction in dhfr gene expression operatively connected to the promoter, and the cells with high level of amplification of vectors containing dhfr gene at low concentration of MTX are selected. As a result, the vector amplification is achieved, and the expression of the foreign protein of purpose is increased at the same time.

According to a preferred embodiment, the promoter sequence used in this invention consists of the nucleotide sequence listed in SEQ ID NO: 1 and SEQ ID NO: 2.

The DHFR-coding nucleotide sequence in the recombinant expression vector is operatively linked to the promoter. The term "operatively linked" used herein refers to functional connection between nucleic acid expression regulation sequence (e.g., promoter sequence) and the other nucleic acid sequence, through the regulation sequence that controls the transcription and/or translation of the other nucleic add sequence.

The DHFR-coding nucleotide sequence used in this invention is preferably a human derived DHFR gene, more preferably human DHFR gene CDC (coding sequence, nucleotide sequence numbers 493-1056) sequence as described in GenBank accession number NM_000791 may be used as the DHRF-coding nucleotide sequence.

The recombinant expression vector of the present invention is used in a dhfr⁻ animal cell. According to the preferred embodiment of the present invention, the animal cell is yeast (Saccharomyces cerevisiae), insect cell or mammalian animal cell, more preferably, a mammalian animal cell, still more preferably, CHO (Chinese hamster ovary) cell line, W138, BHK, COS-7, 293, HepG2, 3T3, RIN, MDCK cell line or BHK (Baby Hamster Kidney) cell line, most preferably, CHO cell line. Since the safety and effectiveness of DHFR-deficient CHO cell has been verified and approved by FDA, the cell line is widely used in producing recombinant protein for clinical use.

According to a preferred embodiment, the expression vector includes an additional nucleotide sequence of a foreign gene.

The foreign gene coding for the target protein to be expressed include any gene sequences. For instance, the foreign gene includes the nucleotide sequence which encodes hormones, hormone analogues, enzymes, enzyme inhibitors, signal transduction proteins or its partial regions, single chain antibodies, binding proteins or its binding domains, antigens, adhesion proteins, structure proteins, regulatory proteins, toxin proteins, cytokines, various regulators, blood clotting factors or vaccine proteins. In detail, the foreign gene amplified and expressed by the vector comprises nucleotide sequences of insulin, IGF-1(insulin-like growth factor 1), growth hormone, BMP (bone morphogenetic protein), TGF (transforming growth factor), erythropoietin, G-CSFs (granulocyte-colony stimulating factors), GM-CSFs (granulocyte/macrophage-colony stimulating factors), interferon-α, interferon-β, interferon-γ, interleukin-1 α and β, interleukin-3, interleukin-4, interleukin-6, interleukin-2, EGFs (epidermal growth factors), calcitonin, ACTH (adrenocorticotropic hormone), TNF (tumor necrosis factor), TNFR (tumor necrosis factor receptor), IDS (iduronate-2-sulfatase), atobisban, buserelin, cetrorelix, deslorelin, desmopressin, dynorphin A (1-13), elcatonin, eleidosin, eptifibatide, GHRH-II (growth hormone releasing hormone-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cydosporin, exedine, lanreotide, LHRH (luteinizing hormone-releasing hormone), nafarelin, parathyroid hormone, pramlintide, T-20 enfuvirtide, thymalfasin or Ziconotide.

According to the preferred embodiment, the upstream nucleotide sequence of the foreign gene is connected by a promoter sequence that can function in a eukaryotic cell. The promoter sequence that can function in the eukaryotic cell is SV40 promoter (SV40 late promoter and SV40 early promoter), tk promoter of HSV (herpes simplex virus), adenovirus 2 major late promoter ($P_{Admi}$), adenovirus 2 early promoter ($P_{AdE2}$), p19 promoter of MV (human parvo virus-associated virus), Epstein-Barr virus (EBV) promoter, Rous Sarcoma virus (RSV) promoter, Vaccinia virus 7.5K promoter, mouse metallothionein promoter, MT promoter, MMTV LTR promoter, HIV LTR promoter, β-actin promoter, EF1 α-promoter, human IL-2 gene promoter, human INF gene promoter, human IL-4 gene promoter, human lymphotoxin promoter, human GM-CSF gene promoter and human hemoglobin, human muscle creatine or human methalotionein derived promoter, but is not limited thereto.

The expression vector of the present invention contains a polyadenylation sequence as the transcription termination sequence, e.g., bovine growth hormone terminator (Gimmi, E. R., et al., *Nucleic Acids Res.* 17:6983-6998(1989)), SV40 derived polyadenylation sequence (Schek, N, et al., *Mol. Cell Biol.* 12:5386-5393(1992)), polyA site of HIV-1 (Klasens, B. I. F., et al., *Nucleic Acids Res.* 26:1870-1876(1998)), polyA site of β-globin (Gil, A., et al, Cell 49:399-406(1987)), polyA site of HSV TK (Cole, C. N. and T. P. Stacy, *Mol. Cell. Biol.* 5:2104-2113(1985)) or polyA site of polyomavirus (Batt, D. B and G. G. Carmichael, *Mol. Cell. Biol.* 15:4783-4790 (1995), but is not limited thereto.

In addition, the expression vector of present invention may contain an antibiotic resistance gene that is known to those of skill in the art as a selective marker gene, e.g., ampicillin, gentamycin, carbenicillin, chloramphenicol, streptomycin, kanamycin, Geneticin (G418), neomycin or tetracycline.

Figure 3A:
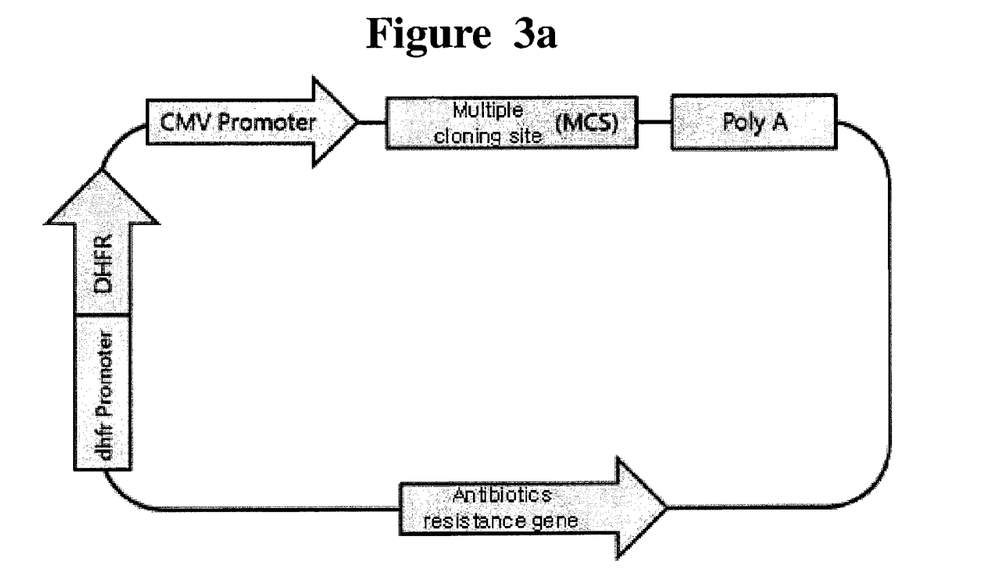
FIG. 3a is a diagram showing the gene map of the recombinant expression vector for an animal cell.

In a more preferably embodiment, the animal cell expression vector for producing high level of foreign protein is a vector with the gene map depicted in FIG. 3, most preferably, the vector is pJK-dhfr-1 (KCTC 11299BP) or pJK-dhfr-2 (KCTC 11300BP).

In one aspect, the present invention provides a dhfr⁻ animal cell line transformed by the dhfr⁻ vector for the animal cell.

The method for transforming animal cell with dhfr⁻ vector includes microinjection method (Capecchi, M. R., *Cell,* 22:479(1980)), calcium phosphate precipitation method (Graham, F. L. et al., *Virology,* 52:456(1973)), electroporation (Neumann, E. et al., *EMBO J.,* 1:841(1982)), liposome-mediated transformation method (Wong, T. K. et al., *Gene,* 10:87(1980)), DEAE-dextran treatment method (Gopal, *Mol. Cell Biol.,* 5:1188-1190(1985)), and gene bombardment (Yang et al., *Proc. Natl. Acad. Sci,* 87:9568-9572(1990)).

In another aspect of this invention, there is provided a method for preparing foreign protein, which comprises (a) a step for culturing the cell line supplemented with dihydrofolate reductase inhibitor to produce large amounts of foreign protein; and (b) a step for purifying the foreign protein from the cell culture medium.

The DHFR inhibitor includes, but not limited to, aminoptrein and methotrexate (MTX). More preferably, the DHFR inhibitor is methotrexate (MTX).

The MTX used in gene amplification is expensive. Even if the amount used for in vitro experiments in labs may not be an important factor, when used in large quantities, it could be an important factor to consider. In addition, it takes more than 6 months for the cells to adjust gradually up to 1 µM of MTX, and cells may show adverse side effect of decreased growth rate when high concentration of MTX is supplemented in the culture medium.

Therefore, there has been ongoing research to reduce the concentration of MTX supplemented in the culture medium. The concentration of MTX conventionally used for gene amplification is 0.05-5 mM. The cell line used in the method for preparation is a transformed cell line which can amplify the gene at low concentrations of MTX. Preferably, the concentration of MTX supplemented in the present invention is 0.001-10 µM, more preferably, 0.003-1 µM, and most preferably 0.005-0.32 µM.

According to the method for preparation, cells may be cultured in any of the conventional animal cell culture mediums, e.g., Eagle's MEM (Eagle's minimum essential medium, Eagle, H. *Science* 130:432(1959)), α-MEM (Stanner, C. P. et al., *Nat. New Biol.* 230:52(1971)), Iscove's MEM (Iscove, N. et al., *J. Exp. Med.* 147:923(1978)), 199 medium (Morgan et al., *Proc. Soc. Exp. Bio. Med.,* 73:1(1950)), CMRL 1066, RPMI 1640 (Moore et al., *J. Amer. Med. Assoc.* 199:519(1967)), F12 (Ham, *Proc. Natl. Acad. Sci. USA* 53:288(1965)), F10 (Ham, R. G. *Exp. Cell Res.* 29:515(1963)), DMEM (Dulbecco's modification of Eagle's medium, Dulbecco, R. et al., *Virology* 8:396(1959)), complex medium of DMEM and F12 (Barnes, D. et al., *Anal. Biochem.* 102:255(1980)), Way-mouth's MB752/1 (Weymouth, C. *J. Natl. Cancer Inst.* 22:1003(1959)), McCoy's 5A (McCoy, T. A., et al., *Proc. Soc. Exp. Biol. Med.* 100:115(1959)) and MCDB series (Ham, R. G. et al., *In Vitro* 14:11(1978)). The medium is described in details in R. Ian Freshney, *Culture of Animal Cells, A Manual of Basic Technique*, Alan R. Liss, Inc., New York, which is incorporated herein by reference in its entity In the cell culturing step, the foreign protein expressed by the host cell is secreted into the culture medium. A large amount of the target protein can be obtained by purifying this secreted protein. The purification step in the present invention may include the conventional purification methods know to those skilled in the art, e.g., solubility fractionation by ammonium sulfate or PEG, ultrafiltration to fractionation by molecular weight, fractionation by various chromatography methods (manufactured to separated based on size, charge, hydrophobicity or affinity), or combination of the above mentioned purification methods.

The features and advantages of the present invention will be summarized as follows:

(i) The present invention provides recombinant vector for a dhfr⁻ animal cell comprising DHFR promoter with reduced promoter activity.

(ii) The vector of the present invention ensures an effective selection of a cell line clone with DHFR gene and foreign gene amplified under low concentrations of methotrexate compared to existing animal cell expression vector.

(iii) The present invention has advantageous effects on cost reduction by using reduced concentration of methotrexate and in the aspect of cell growth rate and productivity.

BRIEF DESCRIPTION OF THE DRAWINGS

In FIG. 3a, DHFR: coding nucleotide sequence of the human derived DHFR; dhfr Promoter: SEQ ID NO: 1 or SEQ ID NO: 2 derived from mouse.

FIG. 11-a is an ELISA analysis result showing the expression level of GS071 antibody in the cell line transformed with pJKIg vector.

FIG. 11-b is an ELISA analysis result showing the expression level of GS071 antibody in the cell line prepared by amplification with 20 nM MTX, and then subcloning.

FIG. 11-c is an ELISA analysis result showing the expression level of GS071 antibody in the cell line prepared by amplification with 80 nM MTX, and then subcloning.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Cloning of Mouse Derived DHFR Promoter, SV40 Early Promoter and SV40 Virus Early Promoter and Enhancer The polymerase chain reaction (PCR) was performed as follows.

First, mouse genomic DNA was isolated using DNA extraction kit (Intron, Korea) ID obtain the DHFR promoter region which is included in the 5'-end sequence of DFHR gene and has strong TATA sequence and basic promoter activity. The mouse derived DHFR promoter was amplified by PCR using 200 ng of isolated mouse DNA, 50 pmol of P1 and P2 primers, 0.5 mM of dNTP and Softmax DNA polymerase (Intron, Korea). The PCR cycle was 29 cycles of denaturation at 1 min at 95° C., 40 sec at 50° C. and 40 sec at 72° C. followed by 10 min at 72° C.

The DNA fragments of early promoter and promoter/enhancer (enhancer operatively linked to the promoter) were amplified by PCR using 10 ng of pcDNA3 vector (Invitrogen, USA) as the template and either P3, P4 and P3, P5 primer sets, respectively. The PCR method (temperature, time and cycle) was similar as the method described above for amplifying mouse derived DHFR promoter. The base sequence of each primers and the size of the DNA fragments obtained by PCR are shown in Table 1.

TABLE 1

| Primer | Base sequence | DNA fragment size |
|---|---|---|
| P1 (SEQ ID NO: 4) | 5'-TCGAAGCTTGATGGCAGCGGGGATAA-3' | 118 bp |
| P2 (SEQ ID NO: 5) | 5'-GGGCTCGAGTAAGCATTGGGGGGGG-3' | 118 bp |
| P3 (SEQ ID NO: 6) | 5'-GATAAGCTTCGAAAAAGGATATACAA-3' | 243 bp |
| P4 (SEQ ID NO: 7) | 5'-CAACTCGAGCATCTCAATTAGTCAGC-3' | 243 bp |
| P3 (SEQ ID NO: 6) | 5'-GATAAGCTTCGAAAAAGGATATACAA-3' | 340 bp |
| P5 (SEQ ID NO: 8) | 5'-CCACTCGAGCCAGGCAGGCAGAAGTA-3' | 340 bp |
| P6 (SEQ ID NO: 9) | 5'-CCCAAAATATGGGGATTGGCAAGAAC-3' | 1462 bp |
| P7 (SEQ ID NO: 10) | 5'-GGGGGATCCGACATGATAAGATACAT-3' | 1462 bp |
| P8 (SEQ ID NO: 11) | 5'-GGGGGATTCACTAGAGCATTGGGGGGGGG GACAGCTCAGGGCTGC-3' | 165 bp |
| P9 (SEQ ID NO: 12) | 5'-CCAATCCCCATATTTTGGGACACGGC-3' | 165 bp |
| P8 (SEQ ID NO: 11) | 5'-GGGGGATCCACTAGAGCATTGGGGGGGGG GACAGCTCAGGGCTGC-3' | 1605 bp |
| P7 (SEQ ID NO: 10) | 5'-GGGGGATCCGACATGATAAGATACAT-3' | 1605 bp |
| P10 (SEQ ID NO: 13) | 5'-GGGGGATCCACAGCTCAGGCTGCGAT-3' | 1583 bp |
| P7 (SEQ ID NO: 10) | 5'-GGGGGATCCGACATGATAAGATACAT-3' | 1583 bp |
| P11 (SEQ ID NO: 14) | 5'-TGCATCTAGATATTCTATAGTGTCAC-3' | 316 bp |
| P12 (SEQ ID NO: 15) | 5'-CCCCAGCTGGTTCTTTCCGCCTCAGAA-3' | 316 bp |

Each of the DNA fragment amplified by PCR was digested with restriction enzymes HindIII and XhoI, purified by GeneClean III Turbo Kit (BIO 101, USA) then subcloned into pGL2-Basic vectors (Promega, USA) which were digested with the same restriction enzymes, to construct pGL2-DHFR vector, pGL2-SV40 promoter vector and pGL2-SV40 promoter/enhancer vector, respectively. The pGL2-Basic vector is a vector encoding the luciferase gene.

Example 2

Comparing the Promoter Activity by Measuring the Expression Level of Luciferase Gene Transcriptionally Regulated by pGL2-DHFR, SV40 Promoter and SV40 Promoter/Enhancer 1) Gene Transfection COS7 cells (ATCC, USA) were plated in DMEM (Dulbecco's Modified Eagle Medium; GIBCO BRL, USA) supplemented with 10% fetal bovine serum and subcultured in a 37° C., 5% $CO_2$ incubator. The cells were plated at a density of $1 \times 10^6$ cells/ml in a 100 mm culture plate and incubated overnight at 37° C., before washing 3 times with OPTI-MEM (osteogenic media I; GIBCO BRL, USA) solution. Meanwhile, 5 μg of pGL2-Basic, pGL2-DHFR, pGL2-SV40P (Promoter) and pGL2-SV40 P/E (Promoter/Enhancer) prepared were each diluted in 500 μl of OPTI-MEM I. Twenty five μl of lipofectamine (GIBCO BRL, USA) was also diluted in 500 μl of OPTI-MEM I. The expression vector and the diluted lipofectamine solution was mixed in a 15-ml tube and incubate at room temperature for 15 min or longer to allow DNA-lipofectamine complex to form. Each of the DNA-lipofectamine complexes was mixed with 5 ml of OPTI-MEM I then added homogeneously onto fresh rinsed COS7 cells. The cells were incubated for 48 hrs in a 37° C., 5% $CO_2$ incubator.

2) Comparison of the Luciferase Expression Levels

The level of luciferase expressed in each vector was analyzed by comparing the activities of the promoters inserted in the vector. After incubating the cells for 48 hrs after the transfection, the cells were washed with 5 ml of PBS. One ml of PBS was added and the cells were collected using a scraper. The cells were centrifugation at 4000 rpm for 5 min at 4° C. and the supernatant was discarded. To lysis the cells, 50 μl of 250 mM Tris (pH 7.8)/1 mM DTT (Dithiothreitol) solution was added, and then submerged in the liquid nitrogen for 1 min before returning to 1 min incubation at 37° C. This procedure was repeated for three times. Then the cell free supernatant were collected after centrifugation for 15 min at 13,000 rpm at 4° C. and stored at −20° C.

Figure 1A:
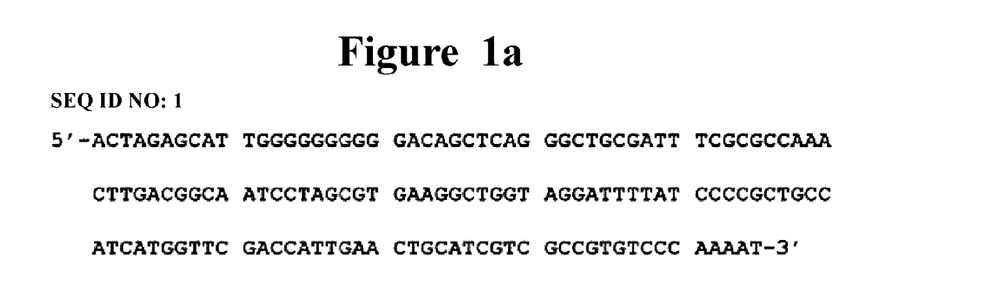
FIG. 1a-1b are DHFR basic promoter sequences (SEQ ID NO:1 and SEQ ID NO:2) used in the present invention.
Figure 1B:
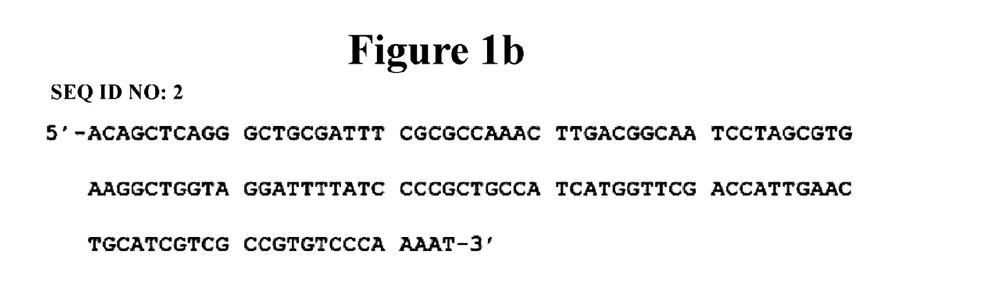
Figure 2:
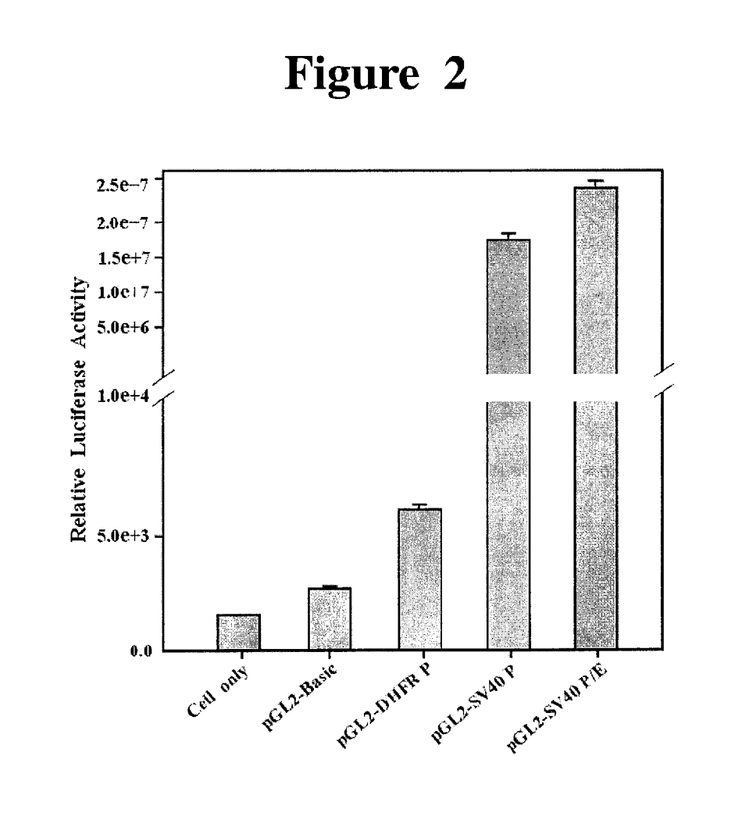
FIG. 2 is the graph comparing the promoter activities through the expression level of luciferase.

The luciferase activity was measured by aliquoting 350 μl of solution A (25 mM glycylglycine (pH 7.8), 0.2 M ATP, 1 M $MgSO_4$, $H_2O$) in a 5 ml (12×75 mm) tube then adding 100 μl each of solution B (25 mM glycylglycine (pH 7.8) and D-luciferin (5 mg/16.5 ml $H_2O$). The tube was inserted in the luminometer for analysis. To measure the luciferase activity, 40 μl of sample solution was added in the solution A and the luciferase activity was measured for 30 sec at 25° C. As a result, the newly selected DHFR basic promoter showed a prominent decrease of 2,300-fold and 3,800-fold lower promoter activities compared to the existing SV40 promoter or SV40 promoter/enhancer (Table 2 and FIG. 2).

TABLE 2

| Vector Used | Luciferase activity |
| --- | --- |
| Cell only | 1,412 |
| pGL2-Basic | 2,457 |
| pGL2-DHFR promoter | 6,346 |
| pGL2-SV40 promoter | 14,713,514 |
| pGL2-SV40 promoter/enhancer | 24,355,978 |

Example 3

Construction of pJK-DHFR-1 Vector

Human genomic DNA was isolated from human blood using DNA extraction kit (Intron, Korea) to clone the DHFR gene. DHFR gene was amplified by PCR using the purified human genomic DNA as a template.

The polymerase chain reaction (PCR) was performed as follows. First, DHFR gene was amplified by PCR using 200 ng of isolated human genomic DNA as the template, 50 pmol of P6 and P7 primers, 0.5 mM of dNTP and Softmax DNA polymerase (Intron, Korea). The PCR cycle was 29 cycles of denaturation at 1 min at 95° C., 40 sec at 55° C. and 40 sec at 72° C. followed by 10 min at 72° C., resulting in amplification of 1462 bp DHFR gene. Mouse DFHR basic promoter was amplified by PCR using pGL2-DFHR as the template and P8 and P9 primer pair, following the PCR method (temperature, time and cycle) similar as described above.

The 3'-region of amplified DHFR basic promoter and the 5'-region of DHFR gene both has conserved 19 bp base sequence region. This conserved region was PCR amplified using P8 and P7 primers, resulting in a 1605 bp DNA fragment, where the basic promoter region and DFHR gene region were connected. The base sequence of each primer and their DNA fragment size amplified by PCR are shown in Table 1.

Figure 3B:
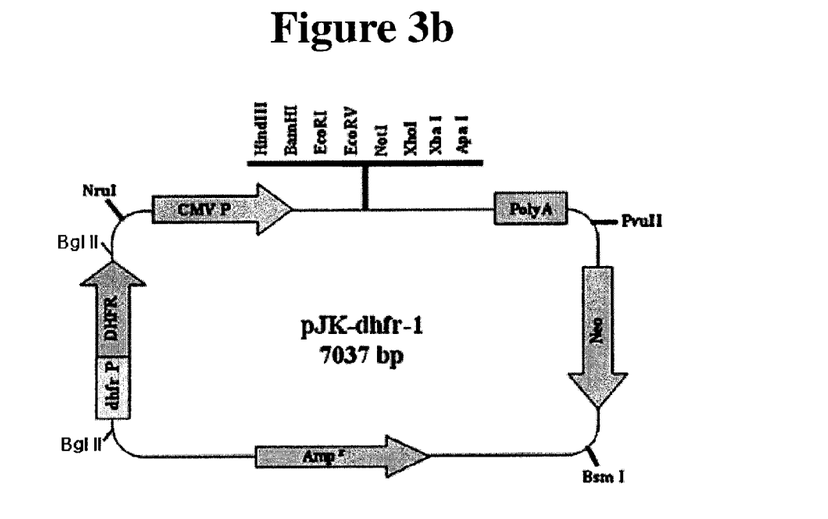
FIG. 3b is a detailed diagram of the recombinant expression vector for the animal cell, pJK-DHFR-1.
Figure 3C:
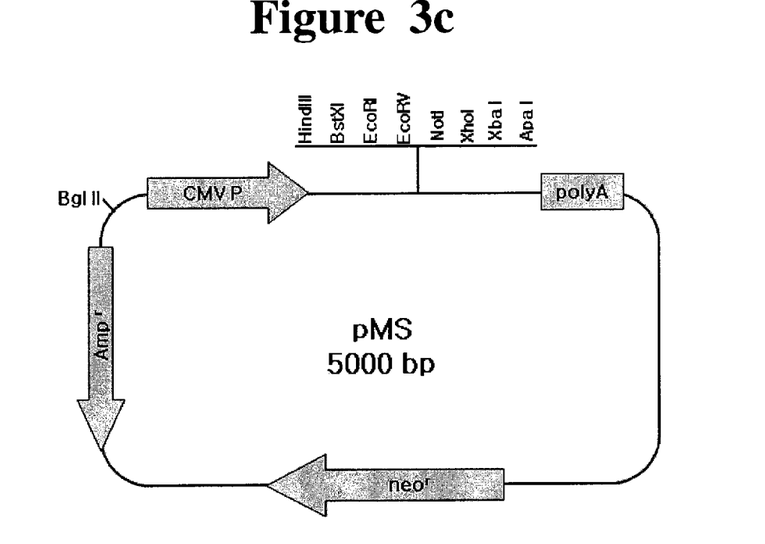
FIG. 3C is a diagram showing the gene map of pMS expression vector used to construct the recombinant expression vector for the animal cell in the present invention.

The DNA fragment of the DHFR promoter and the DHFR gene amplified by PCR was digested with restriction enzyme, BamHI and the pMS vector (Aprogen, Korea) was digested with BglII enzyme. The DHFR promoter and gene were then inserted into the vector to construct pJK-DHFR-1 (FIGS. 3a and 3b). The pJK-DHFR-1 vector was deposited at the gene bank of Korea Research Institute of Bioscience and Biotechnology on Mar. 11, 2008 (deposit No: KCTC 11299BP).

Example 4

Construction of pJK-DHFR-2 Vector

The pJK-DHFR-2 vector was constructed by shortening the DHFR promoter region of pJK-DHFR-1 vector. PCR amplification was performed by the method described in Example 3. The DFHR promoter and DHFR gene were amplified by PCR using pJK-DFHR-1 vector as the template and using P10 and P7 primer pair. The base sequence of each primer and their DNA fragment size amplified by PCR are shown in Table 1.

Figure 4:
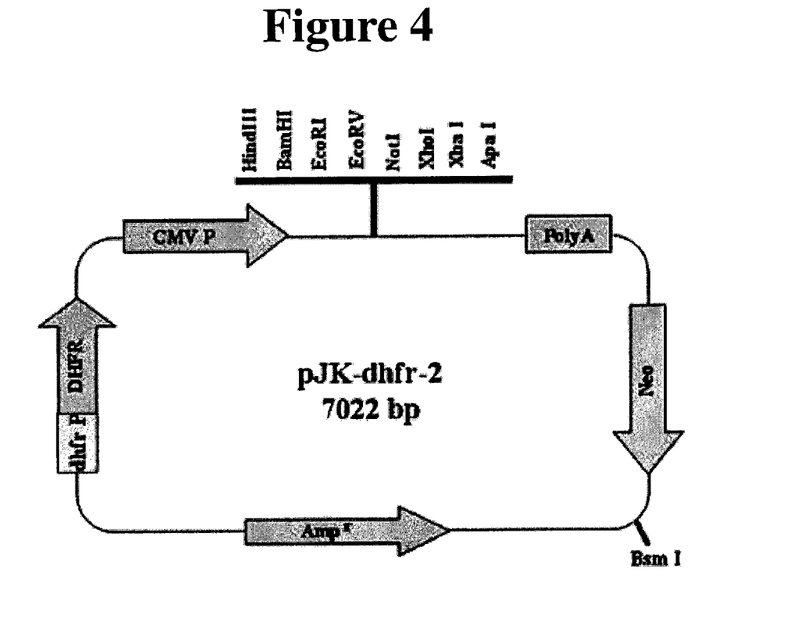
FIG. 4 is a diagram showing the structure of the pJK-DFHR-2 expression vector of the present invention.

The PCR amplified DNA fragment of the DHFR promoter and the DHFR gene were digested with restriction enzyme, BamHI and the pJK-DHFR-1 vector were digested with BglII enzyme. The DHFR promoter and gene were inserted into the vector to construct pJK-DHFR-2 (FIG. 4). The pJK-DHFR-2 vector was deposited at the gene bank of Korea Research Institute of Bioscience and Biotechnology on Mar. 11, 2008 (deposit No: KCTC 11300BP).

Example 5

Construction of pJK-DHFR-Or2 Vector

Figure 5:
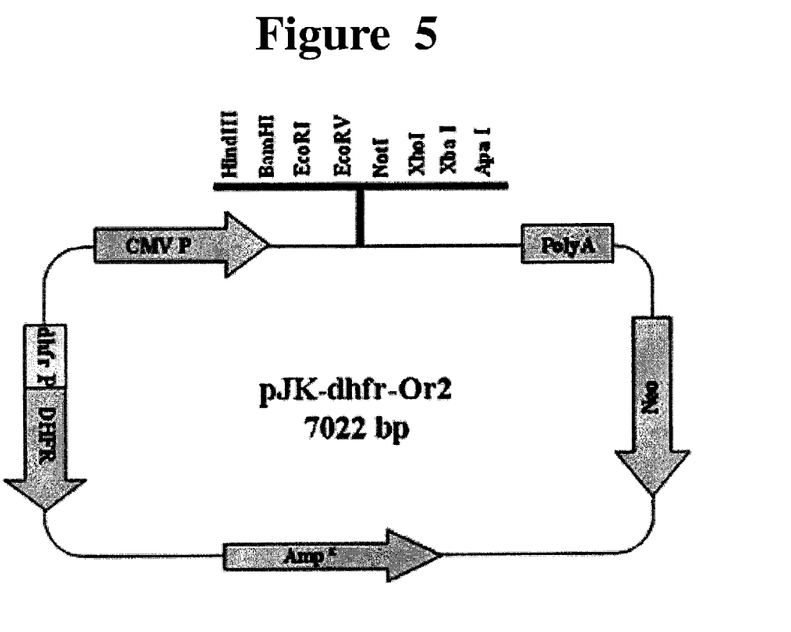
FIG. 5 is a diagram showing the structure of the pJK-DFHR-Or2 expression vector of the present invention.

Following is the method for constructing pJK-DHFR-Or2 vector, which has the DHFR gene in a reverse direction compared to pJK-DHFR-1 vector. As described in Example 3, the DNA fragment of the DHFR promoter and the DHFR gene amplified by PCR was digested with restriction enzyme, BamHI and the pJK-DHFR-1 vector was digested with BglII enzyme. The DHFR promoter and the gene were inserted into the vector, and then screened for the vector that has DHFR gene cloned in the reverse direction. This vector is referred to as pJK-DHFR-Or2. (FIG. 5).

Example 6

Construction of Recombinant Antibody Vector Using pJKIg Vector and pJKIg Vector

The pJKIg vector for cloning the gene for antibody heavy chain and the light chain were constructed using pJK-DHFR-1 vector.

First, the HindIII-BamHI fragment of the pJK-DHFR-1 vector was removed and then ligated by treating with Klenow enzyme (Roche, Switzerland). The XhoI-ApaI fragment was removed from the vector and re-ligated. The vector was prepared by cutting with BsmI and treating with Klenow enzyme.

Figure 6A:
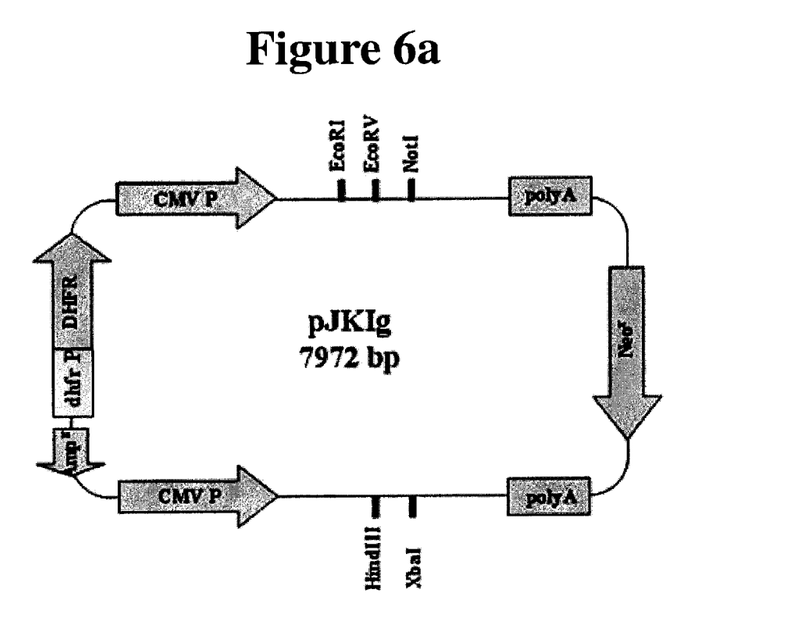
FIGS. 6a-6b are diagrams showing the structure of the pJKIg and pJKIg-RSV HK expression vectors of the present invention.
Figure 6B:
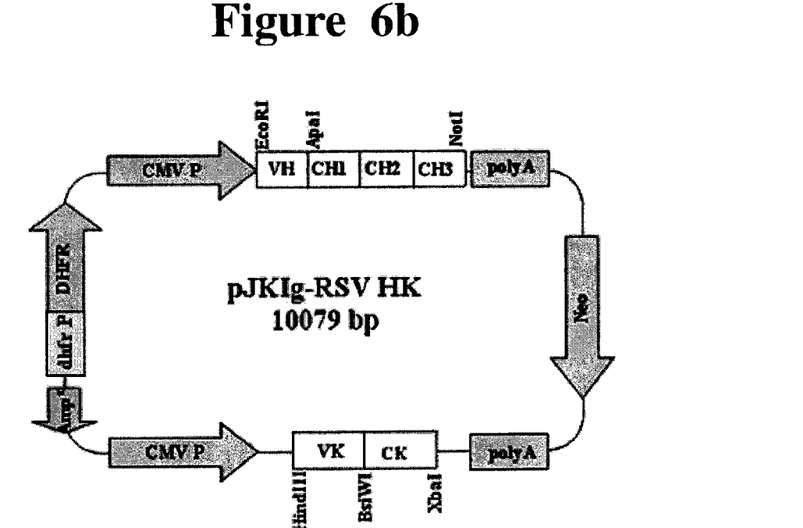

In another pJK-DHFR-1 vector, BamHI-XhoI region in the multiple cloning site was removed, and self-ligated using Klenow enzyme and ligase. To remove the ApaI site on the multiple cloning site, the vector was digested with XbaI and PvuII restriction enzymes. A 316 bp fragment PCR product of the XbaI and PvuII region was PCR amplified using P11 and P12 primer pairs and re-inserted. The pJK-DHFR-1 vector inserted with XbaI and PvuII fragment were digested with NruI-PvuII restriction enzymes to generate a 1075 bp fragment. This fragment was inserted into the above mentioned vector which was digested with BsmI to generate pJKIg vector (FIG. 6a). A pJKIg-RSV HK vector, which has the heavy chain and the light chain of RSV (respiratory syncytial virus) antibody in the pJKIg vector, was constructed as follows. The variable and constant region of immunoglobulin heavy chain in pGEM T/RSV HvHc vector, which is a pGEM T vector (Promega, USA) inserted with a variable and constant region of the antibody heavy chain that interacts with RSV, was digested with EcoRI-NotI enzyme, and then inserted and ligated into pJKIg vector using the same restriction enzyme sites. Similar to the method described above, the constant and variable region of the immunoglobulin light chain in pGEM T/RSV KvKc vector was digested with HinIII-XbaI enzyme, and then inserted into pJKIg vector to construct pJKIg-RSV HK vector (FIG. 6b).

Example 7

Establishment of a Cell Line Producing Recombinant Protein and Antibody to Confirm the Effectiveness of pJK-DHFR and pJKIg Vectors To use the pJK-DHFR vector system, pJK-DHFR-1 and pJK-DHFR-Or2 vectors were digested with EcoRI and XbaI restriction enzymes and inserted with cDNA encoding human derived TNF-R (tumor necrosis factor-receptor) and IDS (iduronate-2-sulfatase) enzyme. The pJKIg-GS051 H/K vector was constructed by cutting the heavy chain region in pJKIg-RSV HK vector with EcoRI and ApaI restriction enzymes and inserting cDNA encoding the heavy chain of GS051 antibody, and cutting the light chain region with HindIII and BsiWI restriction enzymes and replacing with cDNA encoding the light chain region of GS051 antibody. Also, following the method described above, pJKIg-GS071 H/K vector expressing GS071 antibody was constructed.

The vectors expressing the target protein or expressing antibody were each transfected into DHFR gene function deficient CHO DG44 (Columbia University, USA) cells and the cell line was primary selected using antibiotics, G418 (Gibco GRL, USA). The MTX concentration in the selected cell line culture medium was gradually increased to 20, 80, 320 and 1000 nM, the highly productive cell line was selected according to the expression level of target protein or antibody in each clone. The expression level was analyzed by plating each of the selected cell line in a 6-well plate at a density of $5 \times 10^5$ cells and incubating for 3 days. The medium was collected for ELISA (Enzyme-Linked Immunosorbent Assay) analysis. The purified protein with a known concentration was used as a standard.

Figure 7:
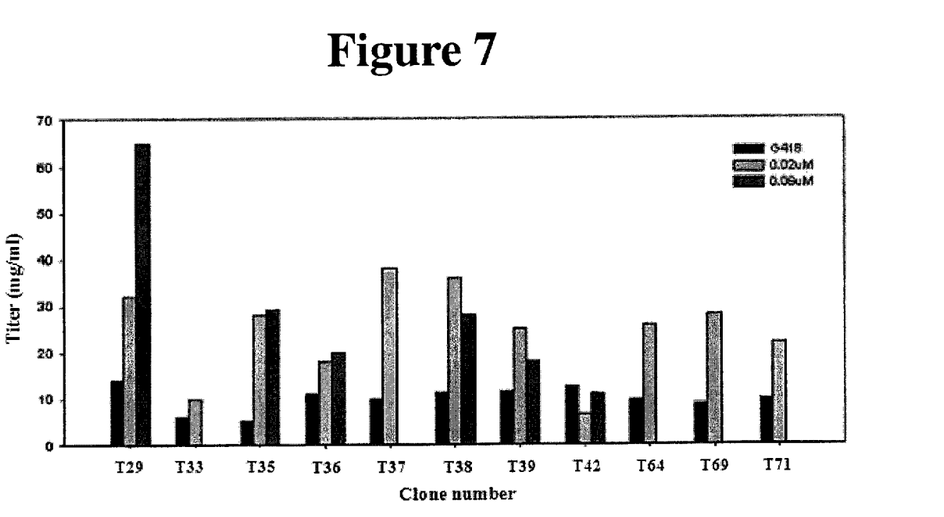
FIG. 7 is an ELISA analysis result showing the expression level of human TNFR in the cell line transformed with pJK-DHFR-1 vector.
Figure 8:
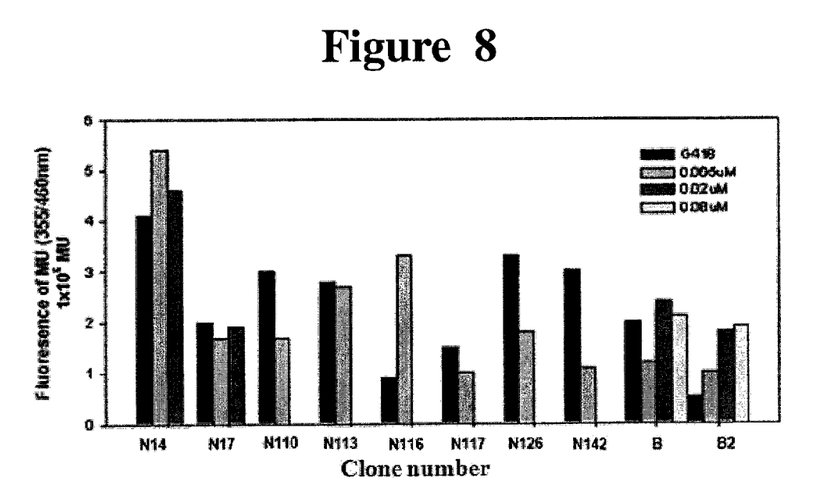
FIG. 8 is an ELISA analysis result showing the expression level of human IDS in the cell line transformed with DHFR-Or2 vector.
Figure 9:
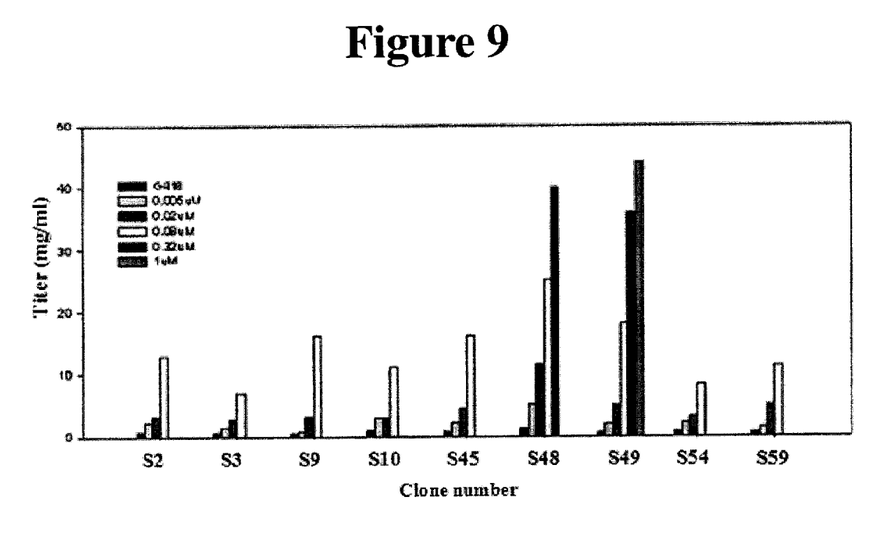
FIG. 9 is an ELISA analysis result showing the expression level of RSV antibody in the cell line transformed with pJKIg vector.
Figure 10:
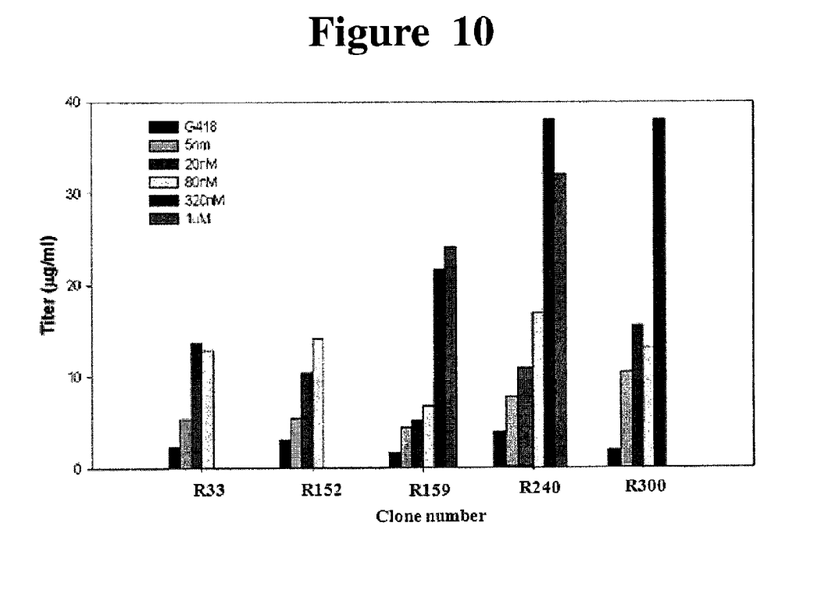
FIG. 10 is an ELISA analysis result showing the expression level of GS051 antibody in the cell line transformed with pJKIg vector.
Figure 11A:
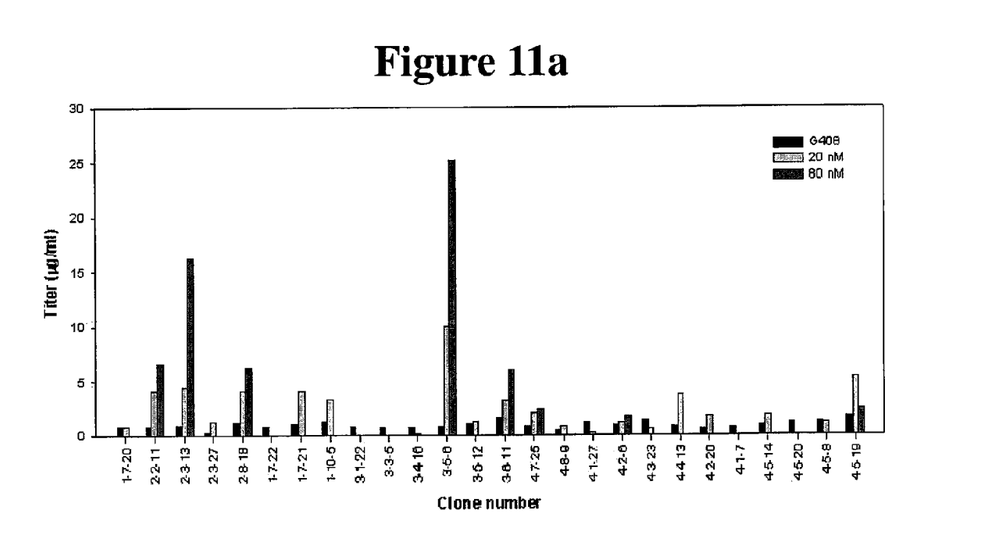
Figure 11B:
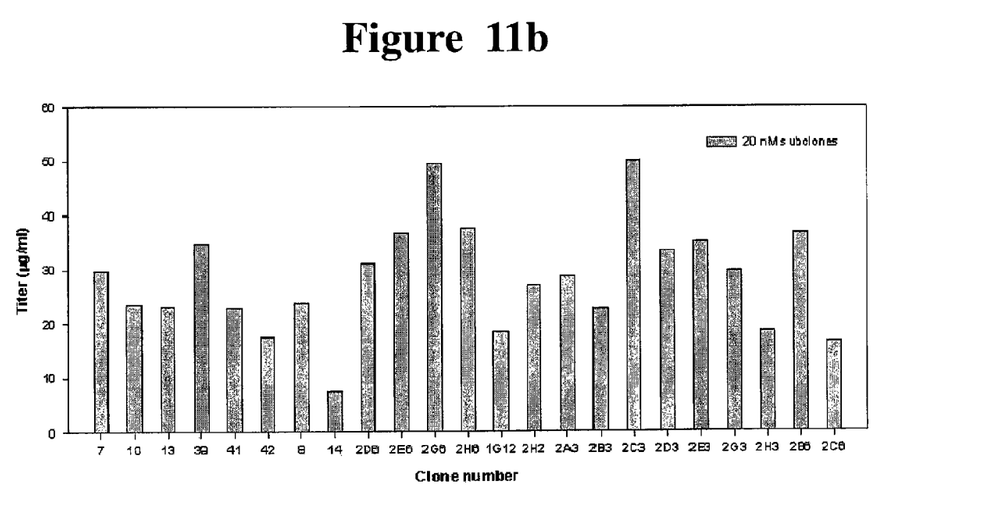
Figure 11C:
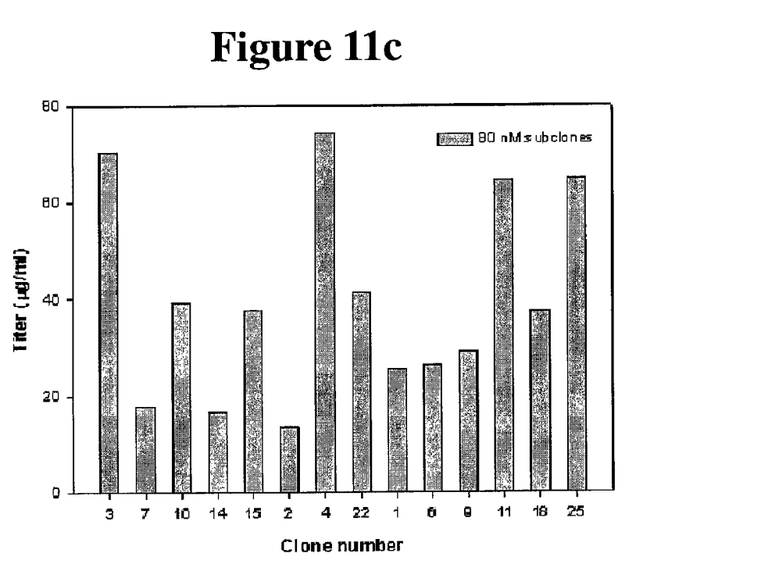

As the result shown in FIG. 7, a highly expressive cell line was selected at 80 nM concentration of MTX. In FIG. 9, a highly expressive cell line was selected at 320 nM and 1 µM concentration of MTX. However, the cell line selected at 1 µM concentration of MTX showed slow cell growth. In FIG. 11, clones 3-5-6 that were amplified and selected at 20 nM and 80 nM of MTX were subcloned and selected for highly expressive cell line. By using a weak DHFR promote and gene, the present inventors provided evidence that the target protein and antibody is highly expressed at 0.005-0.32 µM of low concentrations of MTX compared to the existing MTX concentrations used for expressing the target protein and the antibody.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A recombinant expression vector for a dhfr⁻ (dhfr-deficient) animal cell, comprising:
   (a) a dihydrofolate reductase (DHFR) promoter sequence consisting of the nucleotide sequence of SEQ ID NO:1 or SEQ ID NO:2; and
   (b) a DHFR-coding nucleotide sequence of SEQ ID NO:3 operatively linked to the promoter.

2. The recombinant expression vector for a dhfr⁻ animal cell according to claim 1, wherein the animal cell is a CHO (Chinese hamster ovary) cell.

3. The recombinant expression vector for a dhfr⁻ animal cell according to claim 1, wherein the expression vector comprises additional foreign gene sequence encoding a target protein.

4. The recombinant expression vector for a dhfr⁻ animal cell according to claim 3, wherein the upstream region of the foreign gene sequence is operably linked with a eukaryotic promoter sequence.

5. The recombinant expression vector for a dhfr⁻ animal cell according to claim 1, wherein the expression vector is depicted as the gene map in FIG. 3a.

6. The recombinant expression vector for a dhfr⁻ animal cell according to claim 5, wherein the expression vector is deposited as KCTC 11299BP.

7. The recombinant expression vector for a dhfr⁻ animal cell according to claim 5, wherein the expression vector is deposited as KCTC 11300BP.

8. An isolated animal cell transformed by the recombinant expression vector according to any one of claims 1 and 2-7.

9. A method for preparing a target protein encoded by a foreign gene sequence comprising: (a) culturing an isolated animal cell comprising the recombinant expression vector of claim 3 or claim 4 in the presence of methotrexate; and (b) purifying the target protein from the cell culture.

* * * * *